United States Patent [19]
Lantzsch et al.

[11] Patent Number: 5,998,667
[45] Date of Patent: Dec. 7, 1999

[54] SUBSTITUTED BIPHENYL OXAZOLINES

[75] Inventors: Reinhard Lantzsch, Wuppertal; Albrecht Marhold, Leverkusen; Christoph Erdelen, Leichlingen, all of Germany

[73] Assignee: Bayer Aktiengesellschaft, Leverkusen, Germany

[21] Appl. No.: 09/090,459

[22] Filed: Jun. 4, 1998

Related U.S. Application Data

[62] Division of application No. 08/809,889, filed as application No. PCT/EP95/03787, Sep. 25, 1995.

[30] Foreign Application Priority Data

Oct. 6, 1994 [DE] Germany ............... 44 35 216
Jun. 23, 1995 [DE] Germany ............. 195 23 388

[51] Int. Cl.$^6$ .............. C07C 323/09; C07C 323/18; C07C 323/19; C07C 323/32
[52] U.S. Cl. ............... 564/185; 549/362; 549/365; 549/441; 549/442; 549/443; 549/444; 564/256; 564/337; 568/43; 568/49; 568/52; 568/56
[58] Field of Search ............... 568/38, 39, 43, 568/52, 49, 56; 564/161, 185, 256, 337; 549/362, 365, 441, 442, 443, 444

[56] References Cited

U.S. PATENT DOCUMENTS

| | | | |
|---|---|---|---|
| 2,754,334 | 7/1956 | Battner | 568/39 |
| 3,442,955 | 5/1969 | Newallis | 568/38 |
| 3,901,906 | 8/1975 | Kozlik | 548/238 |
| 4,052,514 | 10/1977 | Adams | 564/161 |
| 5,066,795 | 11/1991 | Umemoto et al. | 540/1 |
| 5,312,930 | 5/1994 | Cheng | 568/39 |
| 5,578,625 | 11/1996 | Suzuki | 514/374 |
| 5,631,014 | 5/1997 | Ishida et al. | 514/374 |
| 5,686,393 | 11/1997 | Lahm et al. | 504/270 |
| 5,767,281 | 6/1998 | Lahm et al. | 548/146 |

FOREIGN PATENT DOCUMENTS

| | | |
|---|---|---|
| 0 345 775 | 12/1989 | European Pat. Off. . |
| 0 432 661 | 6/1991 | European Pat. Off. . |
| 0 594 179 | 4/1994 | European Pat. Off. . |
| 0 645 085 | 3/1995 | European Pat. Off. . |
| 16 43 382 | 3/1971 | Germany . |
| 67 781 | 8/1973 | Luxembourg . |
| WO 93/25079 | 12/1993 | WIPO . |
| WO 95/04726 | 2/1995 | WIPO . |
| WO 96/11190 | 4/1996 | WIPO . |
| WO 98/22448 | 5/1998 | WIPO . |

*Primary Examiner*—Richard L. Raymond
*Attorney, Agent, or Firm*—Sprung Kramer Schaefer & Briscoe

[57] ABSTRACT

The invention relates to new substituted biphenyloxazolines of the formula (I)

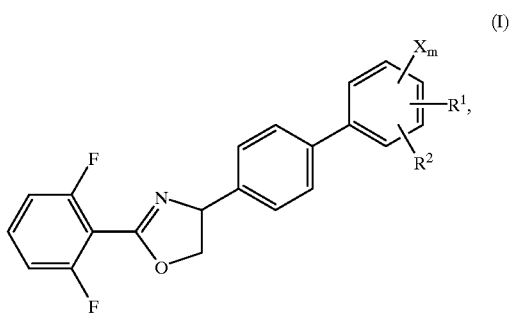

in which

R$^1$ represents C$_1$–C$_6$-halogenoalkylthio and
R$^2$ represents hydrogen, or
R$^1$ and R$^2$ together with the carbon atoms to which they are bonded form a halogen-substituted 5- or 6-membered heterocyclic ring,
X represents hydrogen, halogen, C$_1$–C$_6$-alkyl or C$_1$–C$_6$-alkoxy, and
m represents 0, 1 or 2, to processes for their preparation, to new intermediates, and to the use of the substituted biphenyloxazolines for combating animal pests, with the exception of the compound of the formula

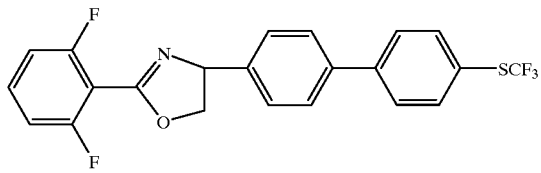

18 Claims, No Drawings

SUBSTITUTED BIPHENYL OXAZOLINES

This is a divisional application of Ser. No. 08/809,889, filed Mar. 31, 1997, now U.S. Pat. No. 5,807,877, which is 371 of PCT/EP95/03787, filed Sep. 25, 1995.

The invention relates to new substituted biphenyloxazolines, to a plurality of processes and intermediates for their preparation, and to their use for combating animal pests.

It has been disclosed that certain substituted biphenyloxazolines, such as 2-(2,6-difluorophenyl)-4-(4'-trifluoromethylthiobiphenyl-4)-2-oxazoline, have an insecticidal and acaricidal activity (cf. WO 95/04726).

However, the level and/or duration of action of this known compound is not entirely satisfactory in all fields of application, in particular when directed against certain organisms or in the case of low use concentrations.

There have been found new substituted biphenyloxazolines of the formula (I)

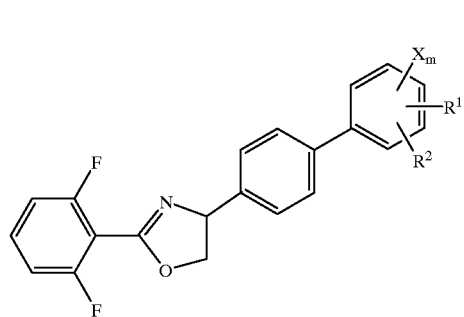

in which

R$^1$ represents C$_1$–C$_6$-halogenoalkylthio and

R$^2$ represents hydrogen, or

R$^1$ and R$^2$ together with the carbon atoms to which they are bonded form a halogen-substituted 5- or 6-membered heterocyclic ring, X represents hydrogen, halogen, C$_1$–C$_6$-alkyl or C$_1$–C$_6$-alkoxy, and m represents 0, 1 or 2, with the exception of the compound of the formula

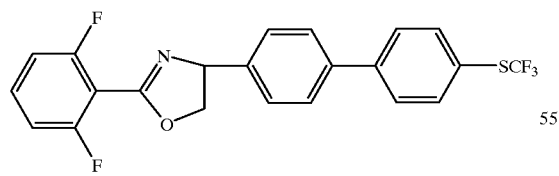

Due to one or more chiral centers, the compounds of the formula (I) are generally obtained in the form of stereoisomer mixtures. They can be used both in the form of their diastereomer mixtures and in the form of the pure diastereomers or enantiomers.

Furthermore, it has been found that the new compounds of the formula (I) are obtained when compounds of the formula (II)

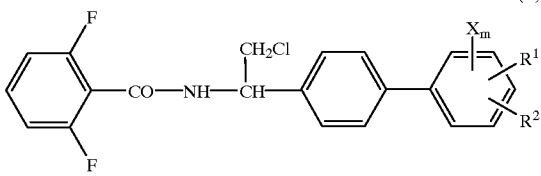

in which

R$^1$, R$^2$, X and m have the abovementioned meanings, are cyclized in the presence of a base, if appropriate in the presence of a catalyst and, if appropriate, in the presence of a diluent (process A).

Furthermore, it has been found that the new substituted biphenyloxazolines of the formula (I) are highly suitable for combating animal pests, in particular insects, arachnids and nematodes, which are encountered in agriculture, in forests, in the protection of stored products and materials, and in the hygiene sector.

Formula (I) provides a general definition of the compounds according to the invention.

Preferred substituents or ranges of the radicals mentioned in the formulae given hereinabove and hereinbelow are illustrated in the following text.

R$^1$ preferably represents C$_1$–C$_4$-halogenoalkylthio, and

R$^2$ represents hydrogen, or

R$^1$ and R$^2$ together with the mutually directly adjacent carbon atoms to which they are bonded form an oxygen-containing 5- or 6-membered ring which is monosubstituted or polysubstituted by fluorine and/or chlorine, X preferably represents fluorine or chlorine, m preferably represents 0 or 1.

R$^1$ particularly preferably represents SCHF$_2$, SCF$_2$CHFCl, SCF$_2$CF$_2$H, SCF$_2$Cl, SCF$_2$Br, SCF$_2$CH$_2$F, SCF$_2$CF$_3$, SCF$_2$CHCl$_2$, SCH$_2$CF$_2$CHF$_2$, SCH$_2$CF$_2$CF$_3$ or SCF$_2$CHFCF$_3$, and R$^2$ represents hydrogen, or R$^1$ and R$^2$ are bonded to directly adjacent carbon atoms and together represent

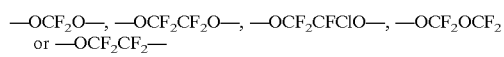

X particularly preferably represents fluorine or chlorine.

m particularly preferably represents 0 or 1.

Very particularly preferred compounds of the formula (I) are those in which R$^1$ is bonded in the 4-position of the phenyl ring.

In each case, the compound of the formula

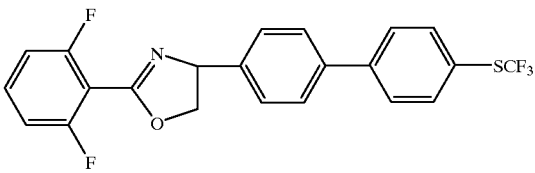

is excepted.

The abovementioned definitions of radicals or illustrations, either in general or where preferred ranges are mentioned, can be combined as desired with each other, that is to say combinations between the ranges and preferred ranges in question are also possible. They apply to the end products and, analogously, to the precursors and intermediates.

Preferred compounds of the formula (I) according to the invention are those in which there exists a combination of the meanings mentioned above as preferred.

Particularly preferred compounds of the formula (I) according to the invention are those in which there exists a combination of the meanings mentioned above as particularly preferred.

If, for example, N-(1-(4-tetrafluoroethylthiobiphenyl-4)-2-chloro-ethyl-1)-2,6-difluorobenzamide is used as starting substance, the course of the process A according to the invention can be represented by the following equation:

sodium hydroxide and potassium hydroxide, and furthermore alcoholates, such as sodium ethanolate or potassium tert-butylate.

If appropriate, the reaction is carried out in the presence of a phase transfer catalyst. Examples of suitable phase transfer catalysts are tertiary ammonium compounds, such as tetraoctylammonium bromide or benzyltriethylammonium chloride.

The temperature can be varied within a substantial range. In general, the process is carried out at temperatures between −10° C. and 150° C., preferably between 0° C. and 100° C.

The reaction is generally carried out under atmospheric pressure.

In general, an equimolar amount of base is employed. If appropriate, however, it is also possible to use an excess of base.

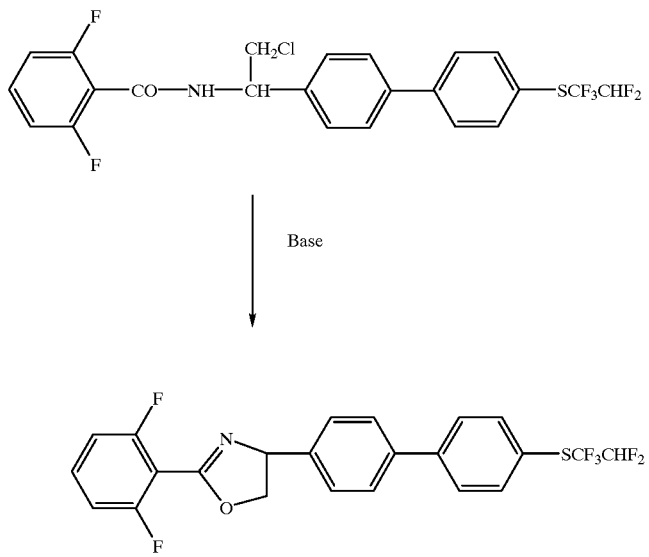

Process A) for the preparation of the compounds of the formula (I) comprises cyclizing the compounds of the formula (II) in the presence of a base, if appropriate in the presence of a catalyst and, if appropriate, in the presence of a diluent.

Cyclization is preferably carried out in the presence of a diluent.

Suitable diluents are all inert organic solvents. If appropriate, they can be used in the form of a mixture with water. Substances which are preferably used are hydrocarbons, such as toluene, xylene, tetralin, hexane, cyclohexane, halogenohydrocarbons, such as methylene chloride, chloroform, chlorobenzene, o-dichlorobenzene, alcohols, such as methanol, ethanol, glycol, the propanol, butanol and pentanol isomers, ethers, such as diethyl ether, diisopropyl ether, dimethoxyethane, tetrahydrofuran, dioxane, nitriles, such as acetonitrile or butyronitrile, amides, such as dimethylformamide, sulfoxides, such as dimethyl sulfoxide, and furthermore sulfolane. Alcohols are particularly preferably used.

Suitable bases are all customary acid acceptors.

Substances which can preferably be used are tertiary amines, such as triethylamine, pyridine, DABCO, DBU, DBN, N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, alkali metal hydroxides, such as Working-up is carried out in the customary manner.

The starting substances of the formula (II) required for the preparation of the compounds of the formula (I) are new; they are obtained when compounds of the formula (III)

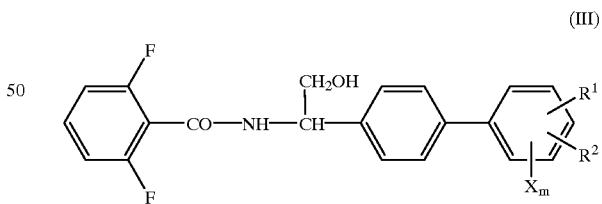

(III)

in which $R^1$, $R^2$, X and m have the abovementioned meanings, are reacted with a chlorinating agent, if appropriate in the presence of a diluent (process B).

If, for example, N-(1-(4'-tetrafluoroethylthiobiphenyl-4)-ethyl-2-ol)-2,6-difluorobenzamide and thionyl chloride are used as starting substances, the course in accordance with process B can be represented by the following equation:

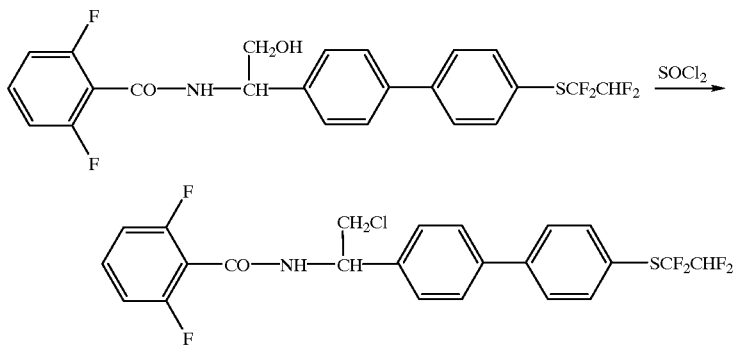

Process B for the preparation of the compounds of the formula (II) comprises reacting compounds of the formula (III) with a chlorinating agent, if appropriate in the presence of a diluent.

Suitable diluents are all inert organic substances. The following are preferably used: hydrocarbons, such as toluene, xylene, hexane, cyclohexane, halogenohydrocarbons, such as chlorobenzene, chloroform, methylene chloride, and ethers, such as diethyl ether, diisopropyl ether, dimethoxyethane, tetrahydrofuran and dioxane.

Suitable chlorinating agents are all reagents which can conventionally be used for this purpose. Examples which may be mentioned are thionyl chloride, phosgene and phosphorus oxychloride, which are generally employed in an at least equimolar amount.

The temperature can be varied within a substantial range. In general, the process is carried out at temperatures between 0° C. and 120° C., preferably between 20° C. and 100° C.

If appropriate, the reaction is carried out in the presence of a base, in particular a tertiary amine, for example triethylamine or pyridine.

The starting substances of the formula (III) are new; they are obtained, for example, when compounds of the formula (IV)

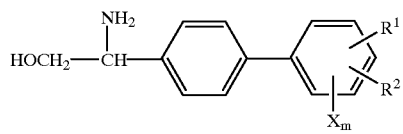

in which $R^1$, $R^2$, X and m have the abovementioned meanings, are reacted with 2,6-difluorobenzoyl chloride, if appropriate in the presence of a base and if appropriate in the presence of a diluent (process C).

If, for example, 2-amino-2-(4'-tetrafluoroethylthiobiphenyl)-4)-ethan-1-ol is used as starting material, the course in accordance with process C can be represented by the following equation:

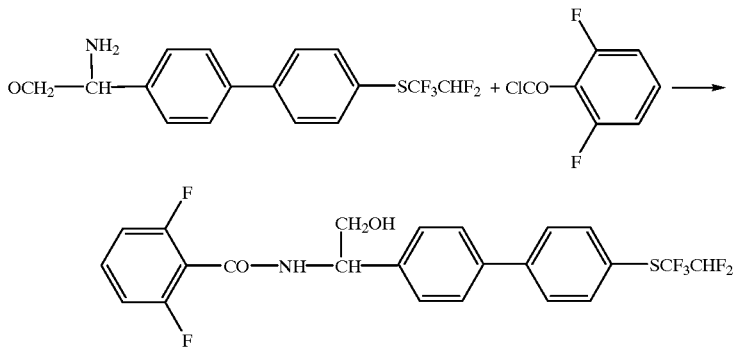

Process C for the preparation of compounds of the formula (III) comprises reacting compounds of the formula (IV) with 2,6-difluorobenzoyl chloride, if appropriate in the presence of a base and if appropriate in the presence of a diluent.

Suitable diluents are all solvents which are inert to these compounds. The following can preferably be used: hydrocarbons, such as benzine, benzene, toluene, xylene and tetralin, furthermore halogenocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulfoxide and sulfolane. If the acid halide is sufficiently stable to hydrolysis, the reaction can also be carried out in the presence of water.

Suitable acid binding agents for the reaction are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, furthermore alkali metal carbonates and alkaline earth metal carbonates, such as sodium carbonate, potassium carbonate and calcium carbonate, and alkali metal hydroxides or alkaline earth metal hydroxides, such as sodium hydroxide or potassium hydroxide.

The reaction temperatures can be varied within a substantial range. In general, the process is carried out at temperatures between −20° C. and +100° C., preferably between 0° C. and 30° C.

The reaction is generally carried out under atmospheric pressure.

When carrying out the reaction, the starting substances of the formula (IV) and 2,6-difluorobenzoyl chloride are generally used in approximately equivalent amounts. However, it is also possible to employ the carboxylic acid halide in a larger excess (up to 5 mol). Working-up is carried out by customary methods.

The starting substances of the formula (IV) are new, they are obtained when compounds of the formula (V)

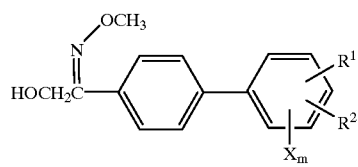

(V)

in which

R$^1$, R$^2$, X and m have the abovementioned meanings are reduced with a reducing agent in the presence of an acid and, if appropriate, in the presence of a diluent (process D).

If, for example, 4-hydroxyacetyl-oxime O-methyl ether 4'-tetrafluoroethylthiobiphenyl is used as starting substance, the course in accordance with process D can be represented by the following equation:

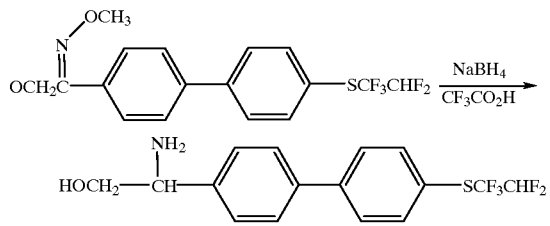

Process D for the preparation of the compounds of formula (IV) comprises reacting the compound of the formula (V) with a reducing agent in the presence of an acid and, if appropriate, in the presence of a diluent.

Suitable diluents are all solvents which are inert to the reactants. The following are preferably used: ethers, such as, for example, diisopropyl ether, methyl tert-butyl ether, tetrahydrofuran, 1,2-dimethoxyethane and dioxane.

The preferred reducing agent is an equimolar amount, or an excess, of sodium boranate.

The preferred acid is an equimolar amount or an excess of trifluoroacetic acid.

The temperature can be varied within a substantial range. In general, the beginning of the reaction is carried out at temperatures between 0° C. and 50° C. and, if appropriate, the temperature is raised during the reaction to up to 120° C.

The reaction is generally carried out under atmospheric pressure.

Working-up is carried out with the aid of customary methods.

The reaction product of the formula (IV) is preferably isolated in the form of salts, for example the hydrochlorides.

The intermediates of the formula (V) are new, they are obtained when compounds of the formula (VI)

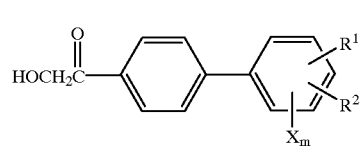

(VI)

in which

R$^1$, R$^2$, X and m have the abovementioned meanings, are reacted with the compound of the formula (VII)

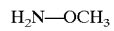

H$_2$N—OCH$_3$     (VII), if appropriate in the presence of a diluent (process E).

If, for example, 4-hydroxyacetyl-4'-tetrafluoroethylthiobiphenyl is used as starting substance, the course in accordance with process E can be represented by the following equation:

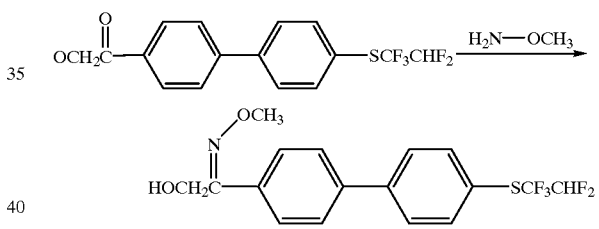

Process E for the preparation of compounds of the formula (V) is characterized in that compounds of the formula (VI) are reacted with the compound of the formula (VII), if appropriate in the presence of a diluent.

Suitable diluents are all customary solvents. Examples of substances which are preferably used are alcohols, such as methanol, ethanol, the propanol, butanol and pentanol isomers, or ethers, such as diisopropyl ether, tetrahydrofuran, dioxane, all of which can optionally be employed in the form of a mixture with water.

O-Methylhydroxylamine, of the formula (VII), can be employed in the form of the free base or else in the form of the salt of an acid. In the latter case, the process is carried out in the presence of a base, preferably sodium acetate. The compound of the formula (VII) is generally employed in equimolar amounts.

The temperature can be varied within a substantial range. In general, the process is carried out at temperatures between −20° C. and 100° C., preferably between 0° C. and 60° C.

The reaction is generally carried out under atmospheric pressure.

Working-up is carried out in the customary manner, for example by filtration or extraction.

The intermediates of the formula (VI) are new, they are obtained when compounds of the formula (VIII)

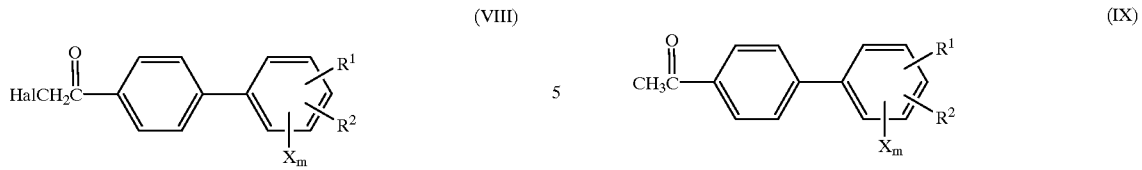

(VIII)

in which

R$^1$, R$^2$, X and m have the abovementioned meanings and

Hal represents chlorine or bromine are reacted with a formic acid salt, if appropriate in the presence of a catalyst (process F).

If 4-chloroacetyl-4'-trifluoromethylthiobiphenyl is used as starting substance, the course in accordance with process F can be represented by the following equation:

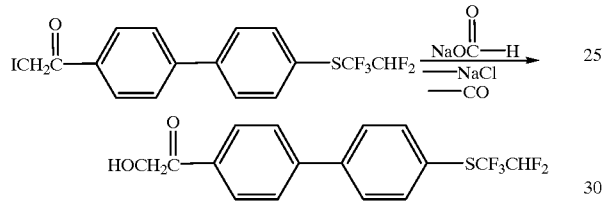

Process F for the preparation of compounds of the formula (VI) comprises reacting compounds of the formula (VIII) with a formic acid salt, if appropriate in the presence of a catalyst.

Suitable diluents are all customary solvents which are inert under the reaction conditions. The following can preferably be used: hydrocarbons, such as toluene, xylene, mesitylene, cyclohexane, methylcyclohexane, chlorohydrocarbons, such as chlorobenzene, o-dichlorobenzene, alcohols, such as methanol, ethanol, the propanol isomers, the butanol and pentanol isomers, ethers, such as diisopropyl ether, tetrahydrofuran, dioxane, nitriles, such as acetonitrile and butyronitrile, amides, such as dimethylformamide, and also strongly polar solvents, such as dimethyl sulfoxide and sulfolane.

If appropriate, the abovementioned diluents can also be used in the form of a mixture with water, if appropriate in the presence of a phase transfer catalyst, such as quaternary ammonium salts, such as tetraoctylammonium bromide or benzyltriethyl-ammonium chloride.

Formic acid salts which can preferably be used are sodium formate and potassium formate.

The temperature can be varied within a substantial range. In general, the process is carried out at temperatures between 50° C. and 200° C., preferably between 80° C. and 160° C.

In general, a procedure is followed in which the compound of the formula (VIII) is heated with 1 to 20 mol, preferably 1 to 5 mol, of formate in a diluent, water is added, if appropriate, and the phases are separated and the diluent is distilled off.

The intermediates of the formula (VIII) are new; they are obtained when compounds of the formula (IX)

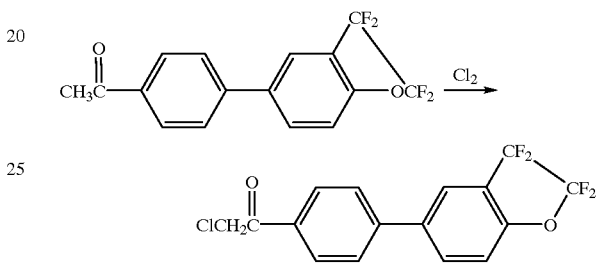

(IX)

in which

R$^1$, R$^2$, X and m have the abovementioned meanings are chlorinated or brominated, if appropriate in the presence of a diluent (process G).

If, for example, 2,2,3,3-tetrafluoro-5-(4-acetylphenyl)-dihydrobenzofuran is used as starting substance, the course in accordance with process G can be represented by the following equation:

Process G for the preparation of compounds of the formula (VIII) comprises chlorinating or brominating compounds of the formula (IX), if appropriate in the presence of a diluent.

Suitable diluents are all solvents which are inert to chlorine and bromine. Examples of substances which are preferably used are chlorohydrocarbons, such as methylene chloride, chloroform or carbon tetrachloride, or alcohols, such as methanol or ethanol.

The temperature can be varied within a substantial range. In general, the process is carried out at a temperature of between −30° C. and 50° C., preferably between −10° C. and 25° C.

The reaction is generally carried out under atmospheric pressure.

In general, a procedure is followed in which the compound of the formula (IX) is introduced into a suitable diluent, and an approximately equimolar amount of chlorine or bromine is then metered in at the temperature desired. A slight excess, or a slightly substoichiometric amount, of halogen can also be employed.

The intermediates of the formula (IX) are new; they are obtained when compounds of the formula (X)

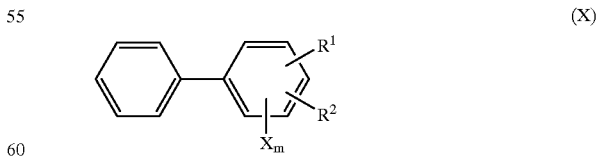

(X)

in which

R$^1$, R$^2$, X and m have the abovementioned meanings are reacted with acetyl chloride, if appropriate in the presence of an acid or Lewis acid and in the presence of a diluent (process H).

If, for example, 2,2-difluoro-5-phenyl-benzodioxole is used as starting substance, the course in accordance with process H can be represented by the following equation:

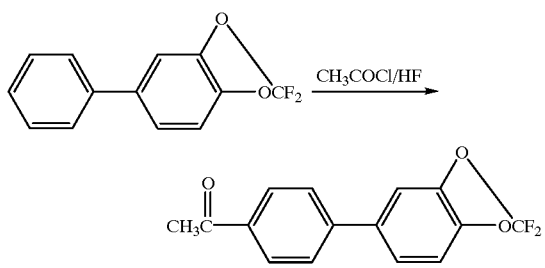

Process H for the preparation of compounds of the formula (IX) comprises reacting compounds of the formula (X) with acetyl chloride and the presence of an acid or Lewis acid and in the presence of a diluent.

Suitable diluents are all customary solvents which are suitable for Friedel-Crafts reactions. Substances which are preferably used are chlorinated hydrocarbons, such as, for example, methylene chloride or dichloroethane, or the process is carried out in an excess of anhydrous hydrofluoric acid.

Suitable acids or Lewis acids are all those which are suitable for Friedel-Crafts reactions. Substances which are preferably used are anhydrous hydrofluoric acid, aluminum chloride, tetrafluoroboric acid or $BF_3$ etherate.

The temperature can be varied within a substantial range. In general, the process is carried out at temperatures between $-30°$ C. and $80°$ C., preferably between $-15°$ C. and $50°$ C.

The reaction is generally carried out under atmospheric pressure or under the elevated pressure which is established when HF is used.

Acetyl chloride and the compounds of the formula (X) are generally employed in approximately equimolar amounts.

After the reaction has ended, the reaction product is worked up with the aid of customary methods.

The intermediates of the formula (X) are new; they are obtained when compounds of the formula (XI)

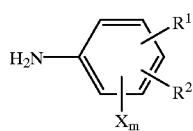 (XI)

in which

R$^1$, R$^2$, X and m have the abovementioned meanings
are diazotized and the diazonium salt formed is reacted with benzene in the presence of an acid and iron powder or in the presence of a base and in each case in the presence of a diluent.

The anilines of the formula (XI) are known and/or can be prepared in a simple manner by known methods. The compounds of the formula (XI) are obtained, for example, by reducing the corresponding nitroaromatics or the corresponding carboxamides, for example by subjecting them to a Hofmann degradation or the like (process I).

If, for example, tetrafluoroethylmercaptoaniline is used as starting substance, the course in accordance with process I can be represented by the following equation:

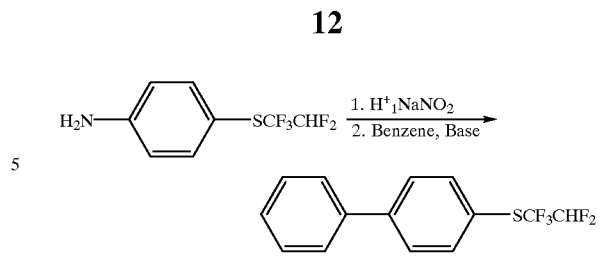

Process I for the preparation of compounds of the formula (X) comprises diazotizing compounds of the formula (XI) and reacting the product with benzene in the presence of acid and iron powder or in the presence of a base and, if appropriate, in the presence of a diluent.

Suitable diluents are all inert solvents. However, a larger excess of the reactant benzene, preferably up to 30 mol, particularly preferably up to 5 mol, relative to the compound of the formula (XI) can also be used as the diluent.

If the reaction is carried out in the presence of acid and iron powder, then suitable acids are organic acids, such as, for example, trichloroacetic acid.

If the reaction is carried out in the presence of a base, then suitable bases are, for example, salts of organic acids, such as alkali metal acetates, in particular sodium acetate or potassium acetate.

In general, two equivalents of base are applied.

The temperature can be varied within a substantial range. In general, the process is carried out at a temperature between $-40°$ C. and $140°$ C., preferably between $-20°$ C. and $80°$ C.

The reaction is generally carried out under atmospheric pressure.

The diazonium salt is generally prepared in the customary manner from the compound of the formula (XI) in the presence of an acid, such as hydrochloric acid or sulfuric acid, by reacting this compound with an alkali metal nitrite, such as sodium nitrite, or an alkyl nitrite, such as pentyl nitrite or methyl nitrite, or by reacting the compound with nitrosyl chloride.

The reaction mixture which contains the product of the formula (X) is worked up with the aid of customary methods.

A further process for the preparation of the intermediates of the formula (VIII) comprises reacting compounds of the formula (X)

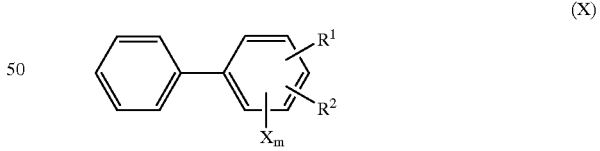 (X)

in which

R$^1$, R$^2$, X and m have the abovementioned meanings
with halogenacetyl chlorides of the formula (XII)

HalCH$_2$COCl  (XII)

in which

Hal represents chlorine or bromine
in the presence of an acid or Lewis acid and in the presence of a diluent (process K)

If, for example, 2,2,4,4-tetrafluoro-6-phenyl-1,3-benzodioxene and chloroacetyl chloride are used as starting substances, the course in accordance with process K can be represented by the following equation:

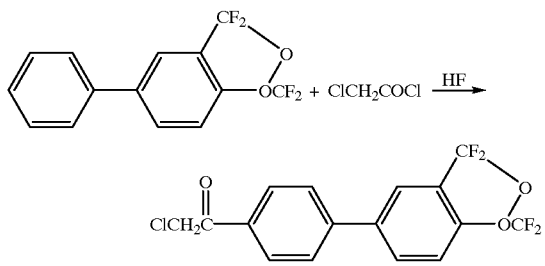

Process K for the preparation of compounds of the formula (VIII) comprises reacting the compounds of the formula (X) with halogenoacetyl chlorides of the formula (XII) in the presence of an acid or Lewis acid and in the presence of a diluent.

Suitable diluents are all customary solvents which are suitable for Friedel-Crafts reactions. Substances which are preferably used are chlorinated hydrocarbons, such as, for example, methylene chloride or dichloroethane, or the process is carried out in an excess of anhydrous hydrofluoric acid.

Suitable acids or Lewis acids are all those which are suitable for Friedel-Crafts reactions. Substances which are preferably used are anhydrous hydrofluoric acid, aluminum chloride or tetrafluoroboric acid.

The temperature can be varied within a substantial range. In general, the process is carried out between $-30°$ C. and $80°$ C., preferably between $-15°$ C. and $50°$ C.

The reaction is generally carried out under atmospheric pressure or under the elevated pressure which is established when HF is used.

The halogenacetyl chloride of the formula (XII) and the compound of the formula (X) are generally employed in approximately equimolar amounts.

After the reaction has ended, the reaction product is worked up with the aid of customary methods.

The starting substances of the formula (III) are also obtained when compounds of the formula (X)

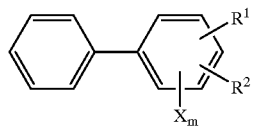
(X)

in which $R^1$, $R^2$, X and m have the abovementioned meanings are reacted with compounds of the formula (XIII)

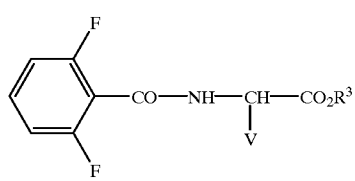
(XIII)

in which

V represents chlorine, hydroxyl or $C_1$–$C_4$-alkoxy and
$R^3$ represents hydrogen or alkyl (preferably $C_1$–$C_6$-alkyl)

in the presence of an acidic catalyst and, if appropriate, in the presence of a diluent, and the resulting compounds of the formula (XIV)

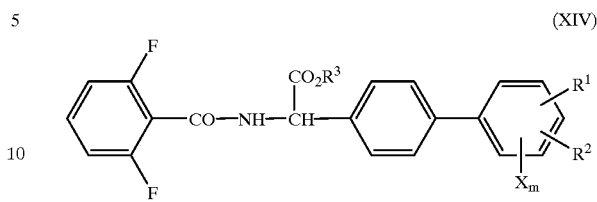
(XIV)

in which $R^1$, $R^2$, $R^3$, X and m have the abovementioned meanings are reduced in the presence of a reducing agent and in the presence of a diluent (process L).

If, for example, N-(carboxymethylchloromethyl)-2,6-difluorobenzamide and 2,2-difluoro-5-phenyl-benzodioxole are used as starting substances, the course in accordance with process L can be represented by the following equation.

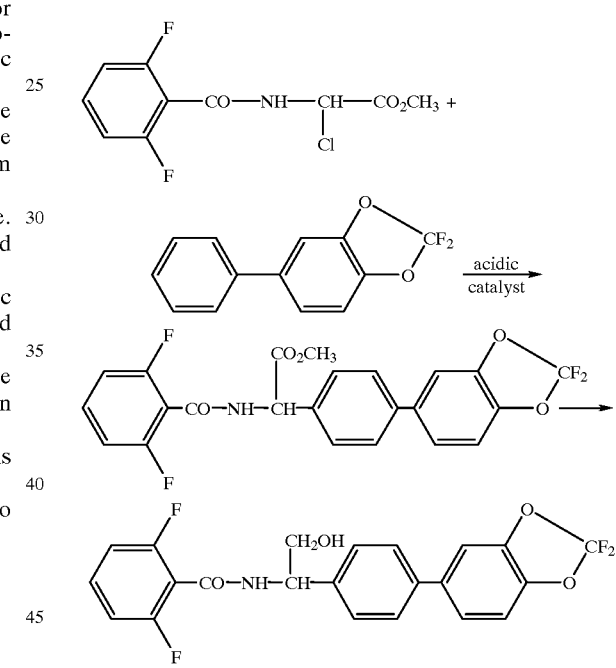

Process L for the preparation of the compound of the formula (III) comprises first reacting the compound of the formula (X) with a compound of the formula (VIII) in the presence of an acidic catalyst, if appropriate, in the presence of a diluent (step 1) and subsequently reacting the resulting compound of the formula (XIV) with a reducing agent in the presence of a diluent (step 2).

Suitable diluents for the first step are all solvents which are inert to the reactants.

Substances which are preferably used are hydrocarbons, such as pentane, hexane, tetralin, halogenohydrocarbons, such as methylene chloride, chloroform, ethers, such as diisopropyl ether, methyl tert-butyl ether, tetrahydrofuran, dioxane, dimethoxyethane or tert-amyl methyl ether.

Suitable acidic catalysts are, in principle, all inorganic or organic acids or Lewis acids. Examples of substances which are preferably used are sulfuric acid, methanesulfonic acid, benzenesulfonic acid, anhydrous hydrofluoric acid, tetrafluoroboric acid, aluminum chloride, titanium tetrachloride, phosphorus oxychloride, boron trifluoride etherate. If appropriate, an excess of acid, can also preferably act as the diluent.

The temperature can be varied within a substantial range. In general, the process is carried out at temperatures between −20° C. and 150° C., preferably between 0° C. and 50° C.

In general, the reaction is carried out under atmospheric pressure or under elevated pressure.

In general, the compound of the formula (X) and the compound of the formula (XIII) are employed in equimolar amounts, however, it is also possible to use an excess of one or the other compound.

Particularly suitable for the second step are alcohols and ethers. Examples which may be mentioned are methanol, ethanol, the propanol, butanol or pentanol isomers, furthermore diethyl ether, diisopropyl ether, methyl tert-butyl ether, tetrahydrofuran, dioxane and dimethoxyethane.

The preferred reducing agent is sodium borohydride in an amount of 1 to 5 mol per mol of the compound of the formula (XIV).

If the compound of the formula (XIV) is in acid form ($R^3$=H), it must be converted into an alkyl ester before reacting with sodium borohydride.

The temperature can be varied within a substantial range. In general, the process is carried out at temperatures between 20° C. and 150° C., preferably between 50° C. and 100° C.

The reaction is generally carried out under atmospheric pressure.

Working-up is carried out with the aid of customary methods.

A further process for the preparation of the compounds of the formula (II) comprises reacting compounds of the formula (X)

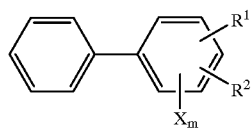

(X)

in which $R^1$, $R^2$, X and m have the abovementioned meanings with compounds of the formula (XV)

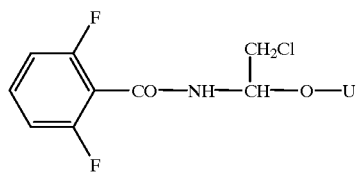

(XV)

in which U represents alkyl (preferably $C_1$–$C_4$-alkyl)

in the presence of a catalyst and, if appropriate, in the presence of a diluent (process M).

If, for example, N-(1-methoxy-2-chloroethyl)-2,6-difluorobenzamide and 4-tetrafluoroethylthiobiphenyl are used as starting substances, the course in accordance with process M can be represented by the following equation:

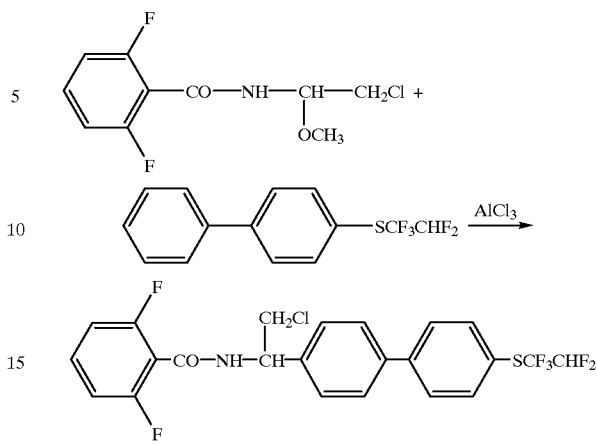

Process M for the preparation of compounds of the formula (II) comprises reacting compounds of the formula (X) with compounds of the formula (XV) in the presence of an acidic catalyst and, if appropriate, in the presence of a diluent.

Suitable diluents are all solvents which are inert to the reactants.

Substances which are preferably used are hydrocarbons, such as pentane, hexane, tetralin, halogenohydrocarbons, such as methylene chloride, chloroform, ethers, such as diisopropyl ether, methyl tert-butyl ether, tetrahydrofuran, dioxane, dimethoxyethane and methyl tert-amyl ether.

Suitable acidic catalysts are inorganic or organic acids or Lewis acids. Examples of preferred substances are sulfuric acid, methanesulfonic acid, benzenesulfonic acid, tetrafluoroboric acid, aluminum chloride, titanium tetrachloride, phosphorus oxychloride, boron trifluoride etherate. If appropriate, an excess of acid can also preferably act as the diluent.

The temperature can be varied within a substantial range. In general, the process is carried out at temperatures between −20° C. and 150° C., preferably between 0° C. and 50° C.

The reaction is generally carried out under atmospheric pressure or under elevated pressure.

The compound of the formula (X) and the compound of the formula (XV) are generally employed in equimolar amounts; however, it is also possible to use an excess of one or the other compound.

The halogenoacetyl chloride of the formula (XII) which are required as starting substances are conventional, generally known chemicals of organic chemistry.

The compound (VII) which is required is a generally known chemical of organic chemistry.

The compounds of the formula (XIII) which are required as starting substances are known and/or can be prepared in a simple manner by known methods (cf., for example, U.S. Pat. No. 5,633,271, which is equivalent to WO 93/24 470).

The compounds of the formula (XV) which are required as starting substances are known and/or can be prepared in a simple manner by customary methods (cf., for example, U.S. Pat. No. 5,354,905 EP-A-0 594 179).

The intermediate of the formulae (X), (IX), (VIII), (VI), (V), (IV), (III), (XIV) and (II) are new and also part of the invention. Some of them have insecticidal and acaricidal properties themselves, for example the compounds of the formulae (III) and (II).

The reaction of certain N-alkoxymethylbenzamide derivatives with benzene derivatives in the presence of, for example, concentrated sulfuric acid or phosphorus oxychloride or anhydrous aluminum chloride to give the corresponding substituted phenylmethylbenzamide derivatives is known (see U.S. Pat. No. 5,354,905 which is equivalent to EP-A-0 594 179).

However, the yields which can be obtained using this known process are not always satisfactory.

There has now been found a new process N for the preparation of compounds of the formula (IIa)

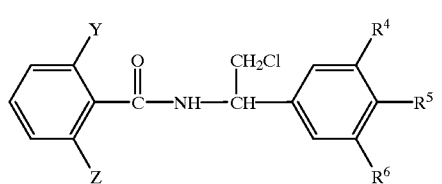
(IIa)

in which
Y represents hydrogen or halogen,
Z represents cyano or halogen,
$R^4$ and $R^6$ independently of one another represent hydrogen, halogen, cyano, nitro, alkyl, alkoxy, halogenoalkyl or halogenoalkoxy,
$R^5$ represents halogen, alkyl, trifluoromethyl, alkoxy, alkylthio, alkoxyalkoxy, alkoxyalkyl, alkenyloxy, alkinyloxy, optionally alkyl-substituted cycloalkyl, one of the radicals

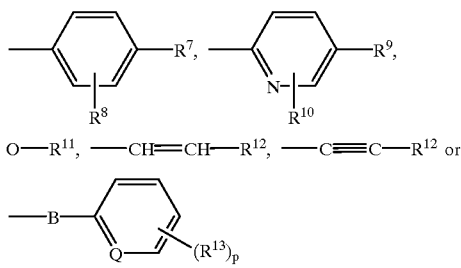

in which
$R^7$ and $R^8$ independently of one another represent hydrogen, cyano, formyl, nitro, $SF_5$, halogen, alkyl, alkoxy, halogenoalkyl, perfluoroalkyl, $S(O)_n$-alkyl, $S(O)_n$-halogenoalkyl, trialkylsilyl, alkylcarbonyl or alkoxycarbonyl or
$R^7$ and $R^8$ together with the carbon atoms to which they are bonded form a halogen-substituted 5- or 6-membered heterocyclic ring,
n represents 0, 1 or 2,
$R^9$ and $R^{10}$ independently of one another represent halogen, alkyl, alkoxy, halogenoalkyl, halogenoalkoxy or trialkylsilyl,
$R^{11}$ represents tetrahydropyranyl, alkyl which is optionally substituted by cyano, alkoxy, alkylcarbonyl, halogenoalkylcarbonyl, alkoxycarbonyl, halogenoalkoxycarbonyl or trialkysilyl, or represents trifluoromethyl, cylcoalkyl, halogenocycloalkyl, cyanocycloalkyl, alkylcycloalkyl, cycloalkylalkyl, halogenocycloalkylalkyl, alkenyl, halogenoalkenyl which is optionally substituted by cyano or alkoxycarbonyl, or phenyl or 2-pyridinyl, each of which is optionally substituted by halogen, alkyl, alkoxy, halogenoalkyl, halogenoalkoxy or trialkylsilyl, or alkinyl, halogenoalkinyl, or represents an 8- to 12-membered bicyclic ring system which has up to 4 hetero atoms selected from amongst 0 to 4 nitrogen atoms, 0 to 2 oxygen atoms and 0 to 2 sulfur atoms and which is optionally substituted by at least one substituent from amongst W,
$R^{12}$ represents phenyl or pyridyl, each of which is optionally substituted by at least one substituent from amongst W,
W represents halogen, cyano, formyl, nitro, $SF_5$, alkyl, halogenoalkyl, alkythio, alkoxy, halogenoalkoxy, alkylcarbonyl or alkoxycarbonyl,
B represents $C_1$–$C_4$-alkylene, $C_1$–$C_4$-alkyleneoxy or $C_1$–$C_4$-alkylenedioxy,
C represents CH or nitrogen,
$R^{13}$ represents halogen, alkyl, alkoxy, halogenoalkyl, halogenoalkoxy or trialkylsilyl and
p represents one of the numbers 1, 2, 3, 4 or 5, where, in the case of p>1, the substituents $R^{13}$ can be identical or different and one substituent $R^{13}$ is always in the para-position relative to B,
which comprises reacting compounds of the formula (XVI)

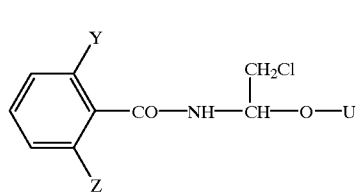
(XVI)

in which
U represents alkyl (preferably $C_1$–$C_4$-alkyl) and
Y and Z have the abovementioned meanings,
with compounds of the formula (XVII)

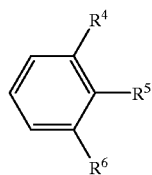
(XVII)

in which
$R^4$, $R^5$ and $R^6$ have the abovementioned meanings
in the presence of anhydrous hydrofluoric acid and, if appropriate, in the presence of a diluent.

Surprisingly, the compounds of the formula (IIa) are obtained by this process in high yield and high purity.

Compounds of the formula (IIa) which are preferably prepared by the process according to the invention are those in which
Y represents hydrogen, fluorine or chlorine,
Z represents fluorine or chlorine,
$R^4$ and $R^6$ independently of one another represent hydrogen, halogen, cyano, nitro, $C_1$–$C_{16}$-alkyl, $C_1$–$C_{16}$-alkoxy, $C_1$–$C_{16}$-halogenoalkyl or $C_1$–$C_{16}$-halogenoalkoxy,
$R^5$ represents fluorine, chlorine, bromine, $C_1$–$C_6$-alkyl, $C_1$–$C_6$-alkoxy or one of the radicals

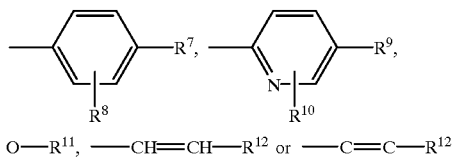

O—R$^{11}$, —CH=CH—R$^{12}$ or —C≡C—R$^{12}$ in which

- R$^7$ and R$^8$ independently of one another represent hydrogen, cyano, formyl, nitro, SF$_5$, halogen, C$_1$–C$_6$-alkyl, C$_1$–C$_6$-alkoxy, C$_1$C$_6$-halogenoalkyl, C$_1$–C$_6$-perfluoroalkoxy, S(O)$_n$—C$_1$–C$_6$-alkyl, S(O)$_n$—C$_1$–C$_6$-halogenoalkyl, Tri-(C$_1$–C$_6$)-alkylsilyl, C$_2$–C$_4$-alkylcarbonyl or C$_2$–C$_4$-alkoxycarbonyl or in which
- R$^7$ and R$^8$ together with the directly adjacent carbon atoms to which they are bonded form an oxygen-containing 5- or 6-membered ring which is monosubstituted or polysubstituted by fluorine and/or chlorine,
- n represents 0, 1 or 2,
- R$^9$ and R$^{10}$ independently of one another represent halogen, C$_1$–C$_6$-alkyl, C$_1$–C$_6$-alkoxy, C$_1$–C$_6$-halogenoalkyl, C$_1$–C$_6$-halogenoalkoxy or tri-(C$_1$–C$_6$-alkyl)-silyl,
- R$^{11}$ represents tetrahydropyranyl, C$_1$–C$_{10}$-alkyl which is optionally substituted by CN, C$_1$–C$_6$-alkoxy, C$_1$–C$_6$-alkylcarbonyl, C$_2$–C$_6$-alkoxycarbonyl, C$_2$–C$_6$-halogenoalkylcarbonyl, C$_2$–C$_6$-halogenoalkoxycarbonyl or tri-(C$_1$–C$_6$-alkyl)-silyl, or represents trifluoromethyl, C$_3$–C$_7$-cycloalkyl, C$_3$–C$_7$-halogenocycloalkyl, cyano-C$_3$–C$_7$-cycloalkyl, C$_4$–C$_7$-aklylcycloalkyl, C$_4$–C$_7$-cycloalkylalkyl, C$_4$–C$_7$-halogenocycloalkylalkyl, C$_3$–C$_8$-alkenyl, C$_2$–C$_{10}$-halogenoalkenyl which is optionally substituted by cyano or C$_2$–C$_6$-alkoxycarbonyl, or phenyl or 2-pyridyl, each of which is optionally substituted by halogen, C$_1$–C$_6$-alkyl, C$_1$–C$_6$-alkoxy, C$_1$–C$_6$-halogenoalkyl, C$_1$–C$_6$-halogenoalkoxy or tri-(C$_1$–C$_6$-alkyl)-silyl, or the C$_3$–C$_6$-alkinyl, C$_3$–C$_{10}$-halogenoalkinyl, or an 8- to 12-membered bicyclic ring system which has up to 4 hetero atoms selected from amongst 0 to 4 nitrogen atoms, 0 to 2 oxygen atoms and 0 to 2 sulfur atoms and which is optionally substituted by at least one substituent from amongst W,
- R$^{12}$ represents phenyl or pyridyl, each of which is optionally substituted by at least one substituent from amongst W, and
- W represents halogen, cyano, formyl, nitro, SF$_5$, C$_1$–C$_3$-alkyl, C$_1$–C$_3$-halogenoalkyl, C$_1$–C$_3$-alkylthio, C$_1$–C$_3$-alkoxy, C$_1$–C$_3$-halogenoalkoxy, C$_2$–C$_4$-alkylcarbonyl or C$_2$–C$_4$-alkoxycarbonyl.

Compounds of the formulae (IIa-a), (IIa-b) and (IIa-c) which can preferably be prepared by the processes according to the invention for the preparation of compounds of the formula (IIa), in addition to the abovementioned compounds of the formula (II), are those which are defined in the following text.

Compounds of the formula (IIa-a)

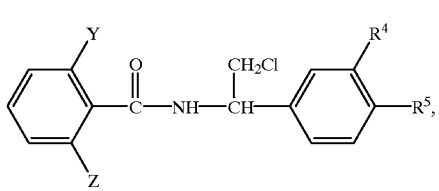

(IIa-a)

in which

- Y represents hydrogen, fluorine or chlorine,
- Z represents cyano, fluorine or chlorine,
- R$^4$ represents hydrogen, halogen, C$_1$–C$_6$-alkyl, C$_1$–C$_6$-alkoxy, trifluoromethyl or trifluromethoxy and
- R$^5$ represents halogen, C$_1$–C$_6$-alkyl, C$_1$–C$_6$-alkoxy, trifluoromethyl or trifluoromethoxy.

Compounds of the formula (IIa-b)

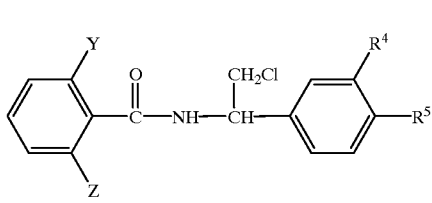

(IIa-b)

in which

- Y represents hydrogen, fluorine or chlorine,
- Z represents fluorine or chlorine,
- R$^4$ represents hydrogen, halogen, C$_1$–C$_6$-alkyl or C$_1$–C$_6$-alkoxy,
- R$^5$ represents C$_7$–C$_{20}$-alkyl, C$_7$–C$_{20}$-alkoxy, C$_1$–C$_{15}$-alkylthio, C$_1$–C$_6$-alkoxy-C$_1$–C$_6$-alkoxy, C$_1$–C$_6$-alkoxy-C$_1$–C$_6$-alkyl, C$_3$–C$_{15}$-alkenyloxy, C$_3$–C$_8$-cycloalkyl which is optionally substituted by C$_1$–C$_6$-alkyl, or C$_3$–C$_6$-alkinyloxy, or the radical

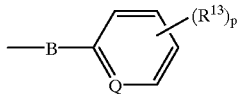

in which

- B represents a direct bond, oxygen, C$_1$–C$_4$-alkylene, C$_1$–C$_4$-alkyleneoxy or C$_1$–C$_4$-alkylenedioxy,
- Q represents CH or nitrogen,
- R$^{13}$ represents halogen, C$_1$–C$_{15}$-alkyl, C$_1$–C$_{15}$-alkoxy, C$_1$–C$_6$-halogenoalkyl, C$_1$–C$_6$-halogenoalkoxy or tri-(C$_1$–C$_6$-alkyl)-silyl and
- p represents one of the numbers 1, 2, 3, 4 or 5, where, in the case that p>1, the substituents R$^{13}$ can be identical or different and one substituent R$^{13}$ is always in the para-position relative to B, and with the proviso that, if Q represents CH and B simultaneously represents a direct bond, R$^{13}$ in its meaning of C$_1$–C$_6$-halogenoalkoxy always represents C$_1$–C$_6$-perfluoroalkoxy.

Compounds of the formula (IIa-c)

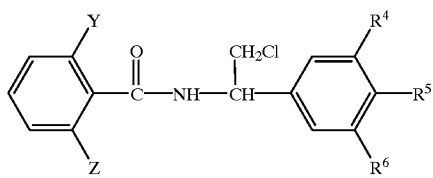

in which

Y represents hydrogen, fluorine or chlorine,

Z represents fluorine or chlorine, $R^4$ and $R^6$ independently of one another represent hydrogen, halogen, cyano, nitro, $C_1$–$C_{16}$-alkyl, $C_1$–$C_{16}$-alkoxy, $C_1$–$C_{16}$-halogenalkyl or $C_1$–$C_{16}$-halogenoalkoxy, $R^5$ represents phenyl which is substituted by at least one substituent from amongst $W^1$ or represents one of the radicals —$OR^{11}$, —CH=CH—$R^{12}$ or —C≡C—$R^{12}$, in which $R^{11}$ represents tetrahydropyranyl, $C_1$–$C_{10}$-alkyl which is optionally substituted by cyano, $C_2$–$C_6$-alkylcarbonyl, $C_2$–$C_6$-halogenoalkylcarbonyl, $C_2$–$C_6$-alkoxycarbonyl, $C_2$–$C_6$-halogenoalkoxycarbonyl or tri-($C_1$–$C_6$-alkyl)-silyl or represents $C_3$–$C_7$-cycloalkyl, $C_3$–$C_7$-halogenocycloalkyl, cyano-$C_3$–$C_7$-cycloalkyl, $C_4$–$C_7$-alkylcycloalkyl, $C_4$–$C_7$-cycloalkylalkyl, $C_4$–$C_7$-halogenocycloalkylalkyl, $C_2$–$C_{10}$-halogenoalkenyl which is optionally substituted by cyano or $C_2$–$C_6$-alkoxycarbonyl, or $C_3$–$C_{10}$-halogenoalkinyl, or an 8- to 12-membered bicyclic ring system which has up to 4 hetero atoms selected from amongst 0 to 4 nitrogen atoms, 0 to 2 oxygen atoms 0 to 2 sulfur atoms and which is optionally substituted by at least one substituent from amongst W, $R^{12}$ represents phenyl which is substituted by at least one substituent from amongst $W^1$, W represents halogen, cyano, formyl, nitro, $SF_5$, $C_1$–$C_3$-alkyl, $C_1$–$C_3$-halogenoalkyl, $C_1$–$C_3$-alkylthio, $C_1$–$C_3$-alkoxy, $C_1$–$C_3$-halogenoalkoxy, $C_2$–$C_4$-alkylcarbonyl or $C_2$–$C_4$-alkoxycarbonyl, $W^1$ represents cyano, formyl, nitro, $SF_5$, $S(O)_n$— $C_1$–$C_3$-alkyl, $S(O)_n$—$C_1$–$C_3$-halogenoalkyl, $C_2$–$C_4$-alkylcarbonyl or $C_2$–$C_4$-alkoxycarbonyl and n represents one of the numbers 0, 1 or 2.

If, for example, N-(1-Methoxy-2-chloroethyl)-2,6-difluorobenzamide and 4-pentafluoroethoxybiphenyl are used as starting substances, the course of process N for the preparation of compounds of the formula (IIa) can be represented by the following equation:

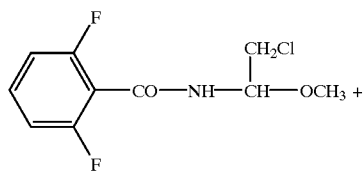

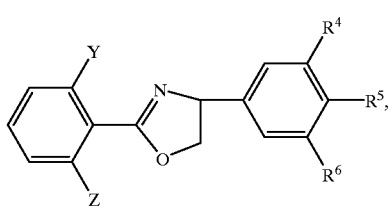

Process N for the preparation of compounds of the formula (IIa) comprises reacting compounds of the formula (XVI) with compounds of the formula (XVII) in the presence of anhydrous hydrofluoric acid and, if appropriate, in the presence of a diluent.

Process N is preferably carried out in the presence of a diluent.

Substances which are preferably used are hydrocarbons, such as pentane, hexane, tetralin, halogenohydrocarbons, such as methylene chloride, chloroform, ethers, such as diisopropyl ether, methyl tert-butyl ether, tetrahydrofuran, dioxane, dimethoxyethane, methyl tert-amyl ether.

The anhydrous hydrofluoric acid can be employed in a substantial excess.

The temperature can be varied within a substantial range. In general, the process is carried out at temperatures between −20° C. and 150° C., preferably between 0° C. and 50° C.

The reaction is generally carried out under atmospheric pressure or under elevated pressure.

The compound of the formula (XVI) and the compound of the formula (XVII) are generally applied in equimolar amounts; however, it is also possible to use an excess of one or the other compound.

In general, a procedure is followed in which an anhydrous hydrofluoric acid and the diluent are introduced into the reaction vessel, the compounds of the formulae (XVI) and (XVII) are added at temperatures around 0° C., and the reaction mixture is stirred in the temperature range given until the reaction has ended. For working-up, excess HF is distilled off, the residue is treated with ice-water, and the product is extracted.

The compounds of the formula (XVI) which are required as starting substances are known (see EP-A-0 594 179).

The compounds of the formula (XVII) which are required as starting substances are known compounds of organic chemistry or can be obtained by known methods (cf., for example, the as yet undisclosed German Patent Application P 44 44 108.8 by the Applicant).

The intermediates of the formula (IIa) can be converted by process A according to the invention to give oxazoline derivatives of the formula (Ia)

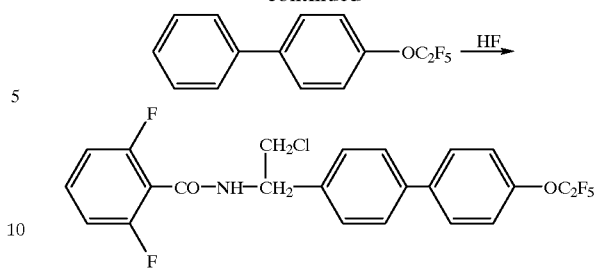

in which

Y, Z, $R^4$, $R^5$ and $R^6$ have the abovementioned meanings which are suitable for combating animal pests (see EP-A-0 345 775, EP-A-0 432 661 and WO 95/04726).

The active compounds of the formula (I) are suitable for combating animal pests, preferably arthropods and nematodes, in particular insects and arachnids, encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The active compounds according to the invention are distinguished by a powerful insecticidal and acaricidal activity.

They can be used particularly successfully for combating insects which are harmful to plants, such as, for example, against the caterpillars of the cabbage moth (*Plutella maculipennis*) or against the caterpillars of the owlet moth (*Spodoptera frugiperda*).

The active compounds can be converted into the customary formulations, such as solutions, emulsions, wettable powders, suspensions, powders, foams, pastes, soluble powders, granules, suspoemulsion concentrates, natural and synthetic materials impregnated with active compound, and very fine capsules in polymeric substances.

These formulations are prepared in a known manner, for example by mixing the active compounds with extenders, that is, liquid solvents, and/or solid carriers, optionally with the use of surface-active agents, that is, emulsifying agents, and/or dispersing agents, and/or foam-forming agents.

In the case of the use of water as an extender, organic solvents can, for example, also be used as auxiliary solvents. As liquid solvents, there are suitable in the main: aromatic compounds, such as xylene, toluene or alkylnaphthalenes, chlorinated aromatic compounds and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkylsulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine colorants, and trace nutrients such as salts of iron, manganese, boron, copper, cobalt, molybdenum and zinc.

The formulations in general comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous components of mixtures are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpicionil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin,
lambda-cyhalothrin, lufenuron,
malathion, mecarbam, mevinphos, mesulfenphos, metaldehyde, methacrifos, methamidophos, methidathion, methiocarb, methomyl, metolcarb, milbemectin, monocrotophos, moxidectin,
naled, NC 184, NI 25, nitenpyram
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
RH 5992,
salithion, sebufos, silafluofen, sulfotep, sulprofos,
tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, YI 5301/5302, zetamethrin.

Herbicides
for example anilides, such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuronethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

The active compound according to the invention can furthermore be present in its commercially available formulations and in the use forms, prepared from these formulations, as a mixture with synergistic agents. Synergistic agents are compounds which increase the activity of the active compounds, without it being necessary for the synergistic agent added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

Preparation and use of the active compounds according to the invention can be seen from the examples below.

PREPARATION EXAMPLES

Example (Ia-1)

Conversion, in accordance with Example (Ia-1), of the intermediate prepared by process N according to the invention into the active compound disclosed in WO 95/04726.

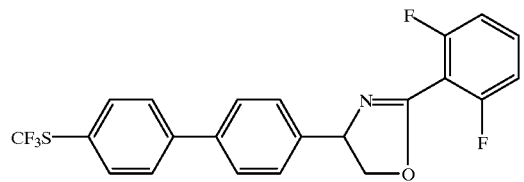

(I-1)

4.4 g (0.01 mol) of 2,6-difluoro-N[-2-chloroethyl-1-phenyl-4-(4'-trifluoromethylthiophenyl)]-benzoic amide of Example (XIV-2) are suspended in 50 ml of methanol.

5.6 g (0.042 mol) of 30% strength sodium hydroxide solution are t hen added, and the mixture is heated for 20 minutes at 70° C. After cooling, the mixture is concentrated, the residue taken up in methylene chloride and the mixture washed three times using water. After drying and concentration, there remain 3.9 g of yellow crystals which are purified over silica gel (petroleum ether/ethyl acetate 1:1). 3.7 g of colorless crystals of m.p. 114° C. are obtained.

Yield: 91.8% of theory.

Example (I-2)

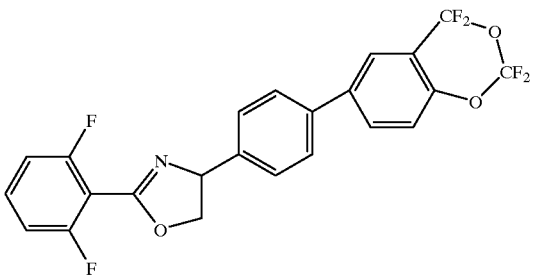

(I-2)

5.19 g (0.01 mol) of the compound of Example (XIV-1) are suspended in 50 ml of dry methanol. 5.33 g (0.04 mol)

of 30% strength sodium hydroxide solution are added dropwise without cooling, resulting in a slightly exothermic reaction. The mixture is heated at the boil for 30 min and cooled. After concentration, the residue is dissolved in ethyl acetate, and the mixture washed three times using water, dried and concentrated. 3.7 g (79.5% of theory) of yellow crystals of m.p. 95–98° C. are obtained.

Example (I-3)

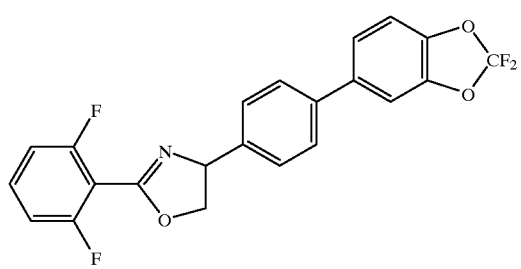

(I-3)

The product is obtained analogously to Example (I-2).

Example (I-4)

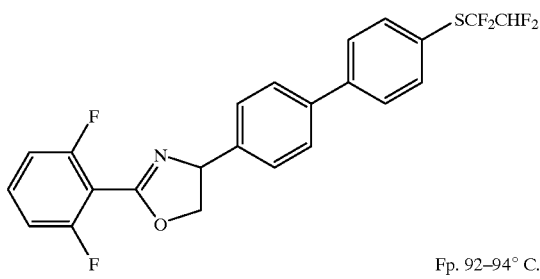

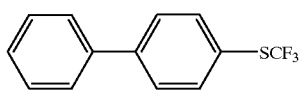

Fp. 92–94° C.

Example (I-5)

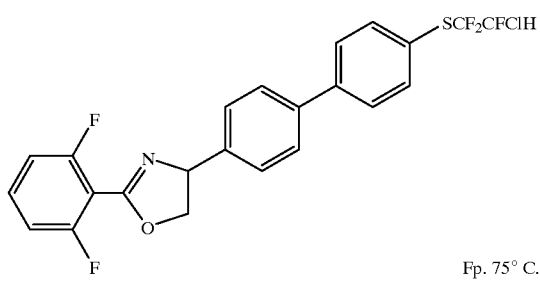

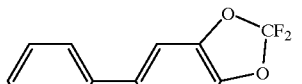

Fp. 75° C.

Preparation of Starting Compounds

Example (X-1)

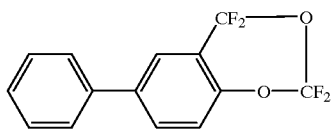

(X-1)

A solution of 750 g of trichloroacetic acid in 1200 ml of benzene is added dropwise in the course of 5 hours at 30–38° C. to 600 ml of benzene, 30 g of Fe powder and 336 g of 2,2,4,4-tetrafluoro-6-amino-benzo-1,3-dioxene, of the formula

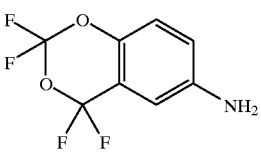

162 g of sodium nitrite are added simultaneously (in portions of 8 g each, every 15 min). After the addition has ended, the mixture is stirred for approximately 20 hours at room temperature. The mixture is subsequently refluxed until the evolution of gas has ceased (approximately 4 hours). After cooling, 1.8 l of 5% strength hydrochloric acid are first added, and excess benzene is then distilled off until an internal temperature of 90° C. has been reached. This is followed by steam distillation. The organic phase is separated off, washed with water, dried and distilled.

108 g of the above compound (X-1) of b.p. (boiling point) 135–141° C./15 mbar are obtained.

The following are obtained analogously and in accordance with the general preparation instructions:

Example (X-2)

(X-2)

M.p.: 47–48° C.

B.p.=140–144° C./20 mbar

Example (X-3)

M.p.: 75° C.

B.p.: 108–115° C. (0.2 mbar)

Example (XIV-1)

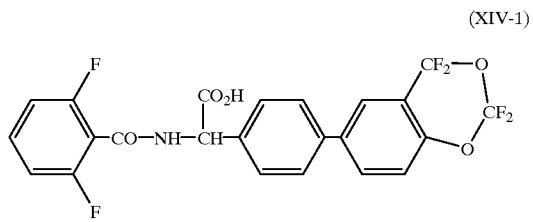
(XIV-1)

11.6 g (0.05 mol) of N-(2,6-difluorobenzoyl)-2-hydroxy-glycine of the formula

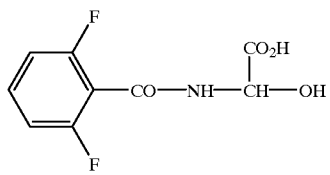

and 90 ml of methanesulfonic acid are mixed at 15° C. 14.2 g (0.05 mol) of 2,2,4,4-tetrafluoro-6-phenyl-1,3-benzodioxene of the formula

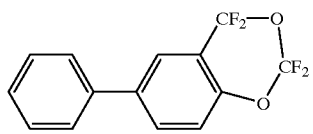

are added and the mixture is stirred for 12 hours at room temperature. The dark brown reaction mixture is poured into 450 ml of ice-water, and the beige precipitate is filtered off, washed with water and dried. 22.3 g (90% of theory) of pale brown crystals of m.p. 193° C. (decomposition) are obtained.

Example (XIV-2)

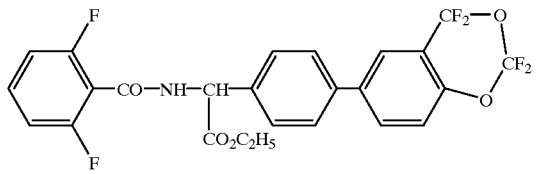
(XIV-2)

21.1 g (0.0425 mol) of product of Example (XIV-1) are introduced into 170 ml of dry ethanol. Starting at room temperature (exothermic reaction), 7 g (0.0585 mol) of thionyl chloride are added dropwise to the clear solution in the course of 10 minutes. The mixture is heated at the boil for 4 hours, cooled and concentrated. 26.7 g of a dark brown oil are obtained which is purified over silica gel (eluent methylene chloride).

Yield: 7.7 g (34.1% of theory) of yellow crystals of m.p. 110–113° C.

Example (III-1)

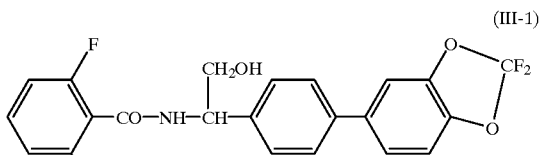
(III-1)

6.5 g (0.028 mol) of α-hydroxy-N-(2,6-difluorobenzoyl)-glycine of the formula

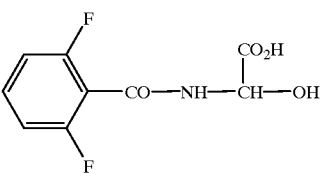

are dissolved in 50 ml of methanesulfonic acid. 6.55 g (0.028 mol) of 5-phenyl-2,2-difluoro-benzodioxole of the formula

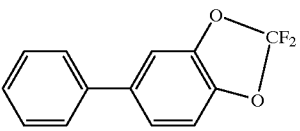

are added at 10° C. The mixture is stirred for 10 hours at room temperature. The brown suspension is poured into 250 ml of ice-water. The beige precipitate is filtered off, washed with water and dried.

The crystals are suspended in 100 ml of ethanol, and 4.5 g of thionyl chloride are added dropwise. The mixture is heated at the boil and held at this temperature for 4 h. It is diluted with 100 ml of water, and the resulting solution is added to 5.32 g (0.14 mol) of sodium borohydride in 50 ml of aqueous ethanol. After the addition has ended, the mixture is heated at the boil for 4 hours, cooled to 5° C., solid is filtered off, the filtrate is treated with 2N hydrochloric acid and extracted three times using methylene chloride, and the organic phase is dried and concentrated.

Yield: 5.3 g (43.6% of theory) of colorless crystals of m.p. 196–201° C.

Example (III-2)

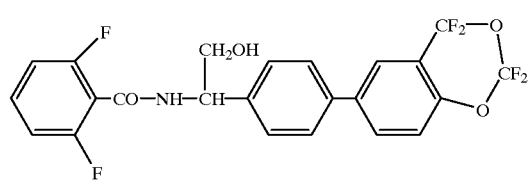
(III-2)

2.5 g (0.0665 mol) of sodium borohydride are introduced into 65 ml of 50% strength aqueous ethanol, 7 g (0.0133 mol) of product of Example (XIV-2) are then added in portions, and the mixture is heated at the boil for 4 hours. It is concentrated slightly, treated with 100 ml of 2N hydrochloric acid, and the solid is filtered off with suction: 6.7 g (72.8% of theory) of white crystals.

Example (II-1)

(II-1)

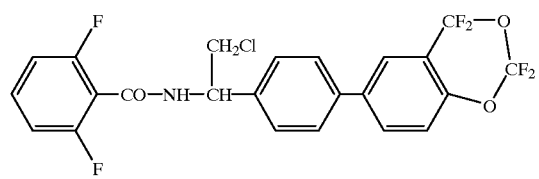

6.5 g (0.0135 mol) of product of Example (III-2) are suspended in 70 ml of dry toluene. Starting at room temperature, 6.4 g (0.054 mol) of thionyl chloride are then added dropwise, and stirring is continued for 3 hours at 70° C. After concentration, there remain 6.6 g of crude product of the formula (II-1) which is employed in Example (I-2) in crude form.

Example (IIa-1)

(IIa-1)

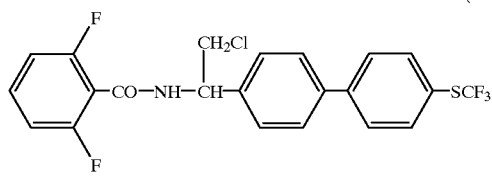

200 g of anhydrous hydrofluoric acid and 100 ml of methylene chloride are introduced into a reaction vessel and cooled to −5° C. A solution of 2.5 g (0.01 mol) of 2,6-difluoro-N-(1-ethoxy-2-chloroethyl)-benzamide of the formula

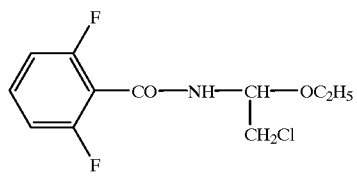

and 3.8 g (0.015 mol) of 4-trifluoromethylthiobiphenyl in 100 ml of methylene chloride are added to this. The mixture is allowed to come to room temperature and stirred for 12 hours at this temperature.

For working-up, excess HF is distilled off and the mixture is poured into ice-water, and the organic phase is separated off, washed with water and concentrated.

After concentration, there remains a crude product which is employed directly in Example (I-1).

The following compounds of the formula (IIa) are obtained analogously to Example (IIa-1) and following the general preparation instructions (II-a)

| Ex.-No. | Y | Z | $R^4$ | $R^5$ | $R^6$ | [° C.] |
|---|---|---|---|---|---|---|
| IIa-2 | F | F | H | | H | 190 |
| IIa-3 | F | F | H | | H | 110–111 |
| IIa-4 | F | F | H | | H | 113 |
| IIa-5 | F | F | H | | H | 110–113 |
| IIa-6 | F | F | H | | H | 126° C. |
| IIa-7 | F | F | H | | H | 162° C. |
| IIa-8 | F | F | H | | H | 146° C. |
| IIa-9 | F | F | H | | H | 129° C. |

The following compounds of the formula (Ia) can be obtained from the compounds of the formula (IIa) by reaction in accordance with process A according to the invention:

| Ex.-No. | Y | Z | R⁴ | R⁵ | R⁶ | [° C.] |
|---|---|---|---|---|---|---|
| Ia-2 | F | F | H | (4-OC₂F₅-phenyl) | H | 117 |
| Ia-3 | F | F | H | (3-CF₃, 4-OCF₃-phenyl) | H | 65–68 |
| Ia-4 | F | F | H | (3-CH₃, 4-CF₃-phenyl) | H | 128–131 |
| Ia-5 | F | F | H | (3-F, 4-OCF₃-phenyl) | H | 106–108 |
| Ia-6 | F | F | H | (3,4-(OCF₂CF₂O)-phenyl) | H | 105 |

The compounds of the formulae Ia-2 to Ia-6 are new. Like the compounds of the formula (I), they are suitable for combating animal pests.

In the use examples which follow, the compound of the formula

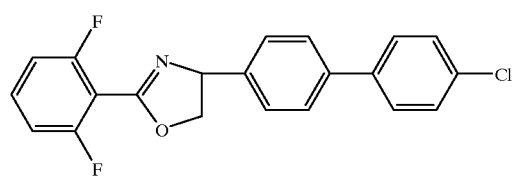

which is disclosed in EP-A 0 432 661 was employed as comparison substance.

Example A

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the cabbage moth (*Plutella maculipennis*) while the leaves are still moist.

After the desired period of time, the destruction in % is determined. 100% means that all the caterpillars have been killed; 0% means that none of the caterpillars have been killed.

In this test, a superior activity relative to the comparison substance was shown, for example, by the compound of Preparation Example (I-2).

Example B

Spodoptera Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), while the leaves are still moist.

After the desired period of time, the destruction in % is determined. 100% means that all the caterpillars have been killed; 0% means that none of the caterpillars have been killed.

In this test, a superior activity relative to the comparison substance was shown, for example, by the compound of Preparation Example (I-2).

We claim:

1. A compound of the formula (X)

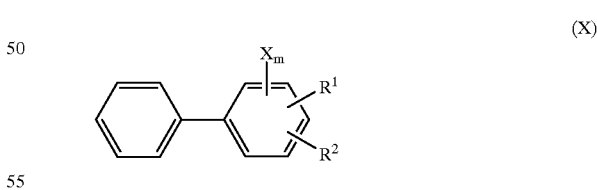

in which $R^1$ represents $C_1$–$C_6$-halogenoalkylthio and $R^2$ represents hydrogen, or $R^1$ and $R^2$ together with the carbon atoms to which they are bonded form a halogen-substituted 5- or 6-membered heterocyclic ring, X represents hydrogen, halogen, $C_1$–$C_6$-alkyl or $C_1$–$C_6$-alkoxy, and m represents 0, 1 or 2 with the exception of the compound of the formula

[Structure: biphenyl-SCF$_3$]

2. A compound of the formula (IX)

(IX)

[Structure: CH$_3$C(O)-C$_6$H$_4$-biphenyl with R$^1$, R$^2$, X$_m$]

in which

R$^1$, R$^2$, X and m have the meanings given in claim 1.

3. A compound of the formula (VIII)

(VIII)

[Structure: HalCH$_2$C(O)-C$_6$H$_4$-biphenyl with R$^1$, R$^2$, X$_m$]

in which

R$^1$, R$^2$, X and m have the meanings given in claim 1 and Hal represents chlorine or bromine.

4. A compound of the formula (VI)

(VI)

[Structure: HOCH$_2$C(O)-C$_6$H$_4$-biphenyl with R$^1$, R$^2$, X$_m$]

in which

R$^1$, R$^2$, X and m have the meanings given in claim 1.

5. A compound of the formula (V)

(V)

[Structure: HOCH$_2$C(=N-OCH$_3$)-C$_6$H$_4$-biphenyl with R$^1$, R$^2$, X$_m$]

in which

R$^1$, R$^2$, X and m have the meanings given in claim 1.

6. A compound of the formula (IV)

(IV)

[Structure: HOCH$_2$-CH(NH$_2$)-C$_6$H$_4$-biphenyl with R$^1$, R$^2$, X$_m$]

in which

R$^1$, R$^2$, X and m have the meanings given in claim 1.

7. A compound of the formula (III)

(III)

[Structure: 2,6-difluorophenyl-CO-NH-CH(CH$_2$OH)-C$_6$H$_4$-biphenyl with R$^1$, R$^2$, X$_m$]

in which

R$^1$, R$^2$, X and m have the meanings given in claim 1.

8. A compound of the formula (XIV)

(XIV)

[Structure: 2,6-difluorophenyl-CO-NH-CH(CO$_2$R$^3$)-C$_6$H$_4$-biphenyl with R$^1$, R$^2$, X$_m$]

in which

R$^1$, R$^2$, X and m have the meanings given in claim 1 and R$^3$ represents alkyl.

9. A compound of the formula (II)

(II)

[Structure: 2,6-difluorophenyl-CO-NH-CH(CH$_2$Cl)-C$_6$H$_4$-biphenyl with R$^1$, R$^2$, X$_m$]

in which

R$^1$, R$^2$, X and m have the meanings given in claim 1.

10. A compound of the formula (X)

(X)

[Structure: biphenyl with X$_m$, R$^1$, R$^2$]

in which $R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy, and
m represents 0, 1 or 2
with the exception of the compound of the formula

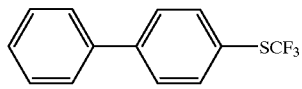

11. A compound of the formula (IX)

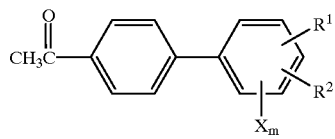
(IX)

in which
$R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy and
m represents 0, 1 or 2.

12. A compound of the formula (VIII)

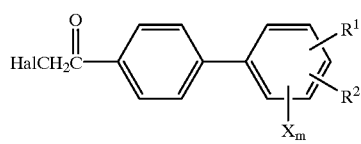
(VIII)

in which
$R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy,
m represents 0, 1 or 2, and
Hal represents chlorine or bromine.

13. A compound of the formula (VI)

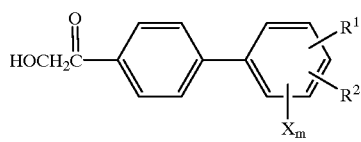
(VI)

in which
$R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy, and
m represents 0, 1 or 2.

14. A compound of the formula (V)

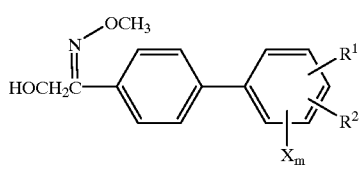
(V)

in which $R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy, and
m represents 0, 1 or 2.

15. A compound of the formula (IV)

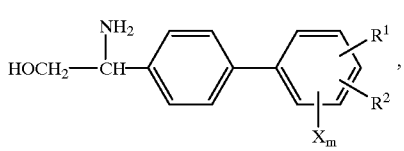
(IV)

in which $R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy, and
m represents 0, 1 or 2.

16. A compound of the formula (III)

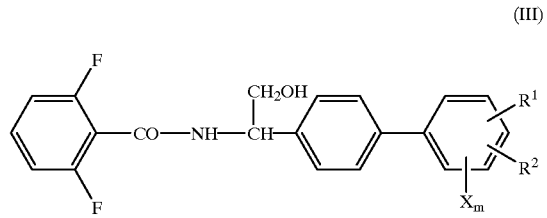
(III)

in which $R^1$ represents $C_1$–$C_6$-halogenoalkylthio and
$R^2$ represents hydrogen,
X represents hydrogen, halogen, $C_1$–$C_6$-alkyl or $C_1$–$C_6$-alkoxy, and
m represents 0, 1 or 2.

17. A compound of the formula (XIV)

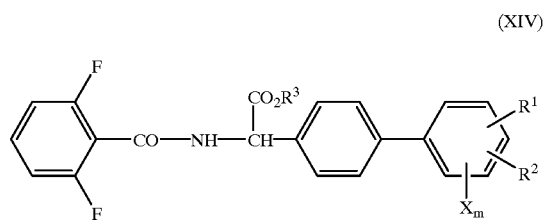

in which

R¹ represents $C_1$–$C_6$-halogenoalkylthio and
R² represents hydrogen,
X represents hydrogen, halogen, $C_1$–$C_6$-alkyl or $C_1$–$C_6$-alkoxy,
m represents 0, 1 or 2, and
R³ represents alkyl.

18. A compound of the formula (II)

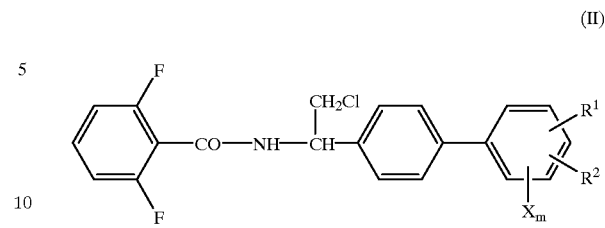

in which

R¹ represents $C_1$–$C_6$-halogenoalkylthio and
R² represents hydrogen,
X represents hydrogen, halogen, $C_1$–$C_6$-alkyl or $C_1$–$C_6$-alkoxy, and
m represents 0, 1 or 2.

* * * * *